United States Patent [19]
Wilson et al.

[11] Patent Number: 5,888,800
[45] Date of Patent: Mar. 30, 1999

[54] EXPRESSION SYSTEMS FOR COMMERCIAL PRODUCTION OF CELLULASE AND XYLANASE IN *BACILLUS SUBTILIS* AND *BACILLUS LICHENIFORMIS*

[75] Inventors: C. Ron Wilson, Santa Rosa; Maria R. Tang, Fairfield; Terri Christianson, Petaluma, all of Calif.; Karl-Heinz Maurer, Erkrath; Albrecht Weiss, Langenfeld, both of Germany

[73] Assignee: Henkel Kommanditgesellschaft auf Aktien, Duesseldorf, Germany

[21] Appl. No.: 694,346

[22] Filed: Aug. 7, 1996

Related U.S. Application Data

[60] Provisional application No. 60/002,106.
[51] Int. Cl.$^6$ .............................. C12N 1/20; C12N 15/00; C12N 9/20; C07H 21/04
[52] U.S. Cl. ................................ 435/252.31; 435/252.33; 435/320.1; 435/200; 435/440; 435/477; 435/485; 536/23.2; 536/23.5; 530/350
[58] Field of Search ........................ 435/252.31, 252.33, 435/320.1, 440, 477, 485, 488, 200

[56] References Cited

U.S. PATENT DOCUMENTS

| | | |
|---|---|---|
| 5,116,746 | 5/1992 | Bernier et al. ........................ 435/172.3 |
| 5,352,604 | 10/1994 | Wilson et al. ........................... 435/221 |

FOREIGN PATENT DOCUMENTS

| | | |
|---|---|---|
| 0265832 | 5/1988 | European Pat. Off. . |
| 0269977 | 6/1988 | European Pat. Off. . |
| 2232983 | 12/1994 | United Kingdom . |
| 94/01532 | 1/1994 | WIPO . |

OTHER PUBLICATIONS

P. Beguin, "Molecular Biology of Cellulose Degradation", Annu.Rev.Microbiol. 1990, 44: pp. 219–248.
Susumu Ito et al. "Alkaline Cellulase for Laundry Detergents: Production by Bacillus sp. KSM–635 and Enzymatic Properties", Agric. Biol. Chem., 53(5), 1989, pp. 1275–1281.
N.R. Gilkes et al., "Bacterial Cellulases", Bioresource Technology 36, (1991) pp. 21–35.
Shitsuw Shikata et al., "Alkaline Cellulases for Laundry Detergents: Production by Alkalophilic Strains of Bacillus and Some Properties of the Crude Enzymes", Agric.Biol.Chem., 54(1), 1990, pp. 91–96.
N. Sumitomo, et al., "Nucleotide Sequence of the Gene for an Alkaline Endoglucanase from an Alkalophilic Bacillus and Its Expression in *Escherichia coli* and *Bacillus subtilis*", Biosci.Biotech.Biochem., 56(6), 1992, pp. 872–877.
K. Horikoshi & F. Fukumori, "Modification and Expression of Alkaline Cellulase Genes of Alkalophilic Bacillus Strains", Biochemistry and Genetics and Cellulose Degradation, Academic Press Limited, 1988, pp. 203–217.
E. Soutschek–Bauer & W.L. Staudenbauer, "Synthesis and secretion of a heat–stable carboxymethylcellulase from *Clostridium thermocellum* in *Bacillus subtilis* and *Bacillus stearothermophilus*", Mol.Gen.Genet. (1987) 208: pp. 537–541.
N. Sashihara, T. Kudo & K. Horikoshi, "Molecular Cloning and Expression of Cellulase Genes of Alkalophilic Bacillus sp. Strain N–4 in *Escherichia coli*", Journal of Bacteriology, May 1984, pp. 503–503.
Fukumori et al., Nucleotide Sequences of Two Cellulase Genes from Alkalophilic Bacillus sp. Strain N–4 and Their Strong Homology, J. Bacteriol., 01 Nov. 1986, vol. 168, No. 2, pp. 479–485.
Fukusaki et al., The Complete Nucelotide Sequence of the Xylanase Gene (xynA) of *Bacillus pumilus*, Federation of European Biochemical Societies Letters, 01 Jun. 1984, vol. 171, No. 2, pp. 197–201.
Lloberas et al., Molecular Cloning, Expression and Nucelotide Sequence of the Endo–β–1,3,–1,4–D–Glucanase Gene From *Bacillus licheniformis*, Eur. J. Biochem., 01 Feb. 1991, vol. 197, No. 2 pp. 337–343.
Pan et al., Expression of the Xylan–Degrading Genes of *Bacillus pumilus* IPO in *Saccharomyces cerevisiae*, J. Ferment. Bioeng., 01 May 1991, vol. 71, No. 5, pp. 303–308.

*Primary Examiner*—Robert A. Wax
*Assistant Examiner*—Tekchand Saidha
*Attorney, Agent, or Firm*—Wayne C. Jaeschke; John E. Drach; Jeffrey S. Steen

[57] ABSTRACT

Increased production of a heterologous cellulase is achieved by transforming *Bacillus subtilis* and *Bacillus licheniformis* with genetic constructs containing a *Bacillus licheniformis* ATCC 53926 protease promoter and signal sequence to express alkalophilic cellulase genes.

12 Claims, 18 Drawing Sheets

P300-CelB Fusion Construct #1

```
AvaI
CTCGGGACCTCTTTCCCTGCCAGGCTGAAGCGGTCTATTCATACTTTCGAACTG  54

AACATTTTTCTAAAACAGTTATTAATAACCAAAAAATTTTAAATTGGTCCTCCA  108
                                                mRNA Start
         StuI
AAAAAATAGGCCTACCATATAATTCATTTTTTTCTATAATAAATTAACAGAAT  162

RBS
AATTGGAATAGATTATATTATCCTTCTATTTAAATTATTCTGAATAAAGAGGAG  216
          Signal Sequence
          Start
GAGAGTGAGTAATGATGAGGAAAAGAGTTTTTGGCTTGGCATGCTGCTCATGA  270
               M  M  R  K  K  S  F  W  L  G  M  L  L  M
                                         Mature Sequence
                                         Start
CACTGGCATTGTTCATTATAGGAAACACGACTGCTGCTGATGATTATTCAGTTG  324
 T  L  A  L  F  I  I  G  N  T  T  A  A  D  D  Y  S  V TAGAGGAGCATGGGCAATTAAGTATTAGTAACGGAGAATTAGTCAATGATCGAG  378
 V  E  E  H  G  Q  L  S  I  S  N  G  E  L  V  N  D  R XmnI
GCGAACCAGTTCAGTTAAAAGGGATGAGTTCCCATGGTTTACAATGGTACGGTC  432
 G  E  P  V  Q  L  K  G  M  S  S  H  G  L  Q  W  Y  G AATTTGTAAACTATGAAAGCATGAAATGGCTAAGAGATGATTGGGGTATAACTG  486
 Q  F  V  N  Y  E  S  M  K  W  L  R  D  D  W  G  I  T TATTCCGAGCAGCGATGTATACATCTTCGGGAGGATATATTGAGGATCCTTCCG  540
 V  F  R  A  A  M  Y  T  S  S  G  G  Y  I  E  D  P  S TAAAGGAAAAAGTAAAAGAGGCTGTTGAGGCTGCGATAGACCTTGGTATATATG  594
 V  K  E  K  V  K  E  A  V  E  A  A  I  D  L  G  I  Y TCATAATTGATTGGCACATCCTTTCAGACAATGACCCGAATATATATAAAGAAG  648
 V  I  I  D  W  H  I  L  S  D  N  D  P  N  I  Y  K  E
```

FIG. 7

```
AAGCAAAGGATTTCTTTGATGAAATGTCTGAGCTGTATGGAGATTACCCGAATG 702
 E   A  K  D  F  F  D  E  M  S  E  L  Y  G  D  Y  P  N

TGATATACGAAATTGCAAATGAACCGAATGGTAGTGATGTTACGTGGGACAATC 756
 V  I  Y  E  I  A  N  E  P  N  G  S  D  V  T  W  D  N

Xmnl
AAATAAAACCGTATGCAGAGGAAGTAATTCCGGTTATCCGTAACAATGATCCTA 810
 Q  I  K  P  Y  A  E  E  V  I  P  V  I  R  N  N  D  P ATAACATTATTATTGTAGGTACAGGTACATGGAGTCAGGATGTTCATCATGCTG 864
 N  N  I  I  I  V  G  T  G  T  W  S  Q  D  V  H  H  A CTGATAATCAGTTAACAGATCCGAACGTCATGTATGCATTTCATTTTTATGCAG 918
 A  D  N  Q  L  T  D  P  N  V  M  Y  A  F  H  F  Y  A GAACACATGGACAAAATTTACGAGACCAAGTAGATTATGCATTAGATCAAGGAG 972
 G  T  H  G  Q  N  L  R  D  Q  V  D  Y  A  L  D  Q  G CAGCAATATTTGTTAGTGAATGGGGAACGAGTGAAGCTACTGGTGATGGCGGCG 1026
 A  A  I  F  V  S  E  W  G  T  S  E  A  T  G  D  G  G TGTTTTTAGATGAAGCACAAGTGTGGATTGACTTTATGGATGAAAGAAATTTAA 1080
 V  F  L  D  E  A  Q  V  W  I  D  F  M  D  E  R  N  L GCTGGGCAAACTGGTCTCTAACGCACAAAGATGAGTCATCTGCGGCGTTAATGC 1134
 S  W  A  N  W  S  L  T  H  K  D  E  S  S  A  A  L  M CAGGTGCAAGCCCAACTGGTGGGTGGACAGAGGCTGAACTATCTCCATCTGGGA 1188
 P  G  A  S  P  T  G  G  W  T  E  A  E  L  S  P  S  G CATTTGTGAGGGAAAAAATAAGAGAGTCAGCAACAACACCACCTAGTGATCCAA 1242
 T  F  V  R  E  K  I  R  E  S  A  T  T  P  P  S  D  P
```

FIG. 7A

```
CACCACCATCTGATCCAGATCCAGGTGAACCAGAACCAGATCCAGGTGAACCGG  1296
 T  P  P  S  D  P  D  P  G  E  P  E  P  D  P  G  E  P

ATCCAACGCCACCAAGTGATCCAGGAGATTATCCGGCATGGGATCCAAATACAA  1350
 D  P  T  P  P  S  D  P  G  D  Y  P  A  W  D  P  N  T

TTTATACAGATGAAATTGTGTACCATAACGGCCAGCTATGGCAAGCAAAATGGT  1404
 I  Y  T  D  E  I  V  Y  H  N  G  Q  L  W  Q  A  K  W

RsrII              Mature End
GGACGCAAAATCAAGAGCCAGGCGACCCATACGGTCCGTGGGAACCACTCAATT  1458
 W  T  Q  N  Q  E  P  G  D  P  Y  G  P  W  E  P  L  N

AACGATATAATGATAGAAATTTACTAATGATATAAGGAGAATGCCAAGAGTCTA  1512
  -

KpnI        SstI
AATTGGACGATTGGCATTCTCATGGTACCTATTAGAGCTC
```

FIG. 7B

P300-CelB Fusion Construct #2

```
AvaI
CTCGGGACCTCTTTCCCTGCCAGGCTGAAGCGGTCTATTCATACTTTCGAACTG  54

AACATTTTTCTAAAACAGTTATTAATAACCAAAAAATTTTAAATTGGTCCTCCA  108
                                            mRNA Start
     StuI                                       ────▶
AAAAAATAGGCCTACCATATAATTCATTTTTTTCTATAATAAATTAACAGAAT  162

RBS
AATTGGAATAGATTATATTATCCTTCTATTTAAATTATTCTGAATAAAGAGGAG  216
      Signal Sequence
      Start ────▶       BglII
GAGAGTGAGTAATGATGAGGAAAAAGATCTCTACTATTTTGTCGTATTGCTCA  270
           M  M  R  K  K  I  S  T  I  F  V  V  L  L
                              Mature Sequence
                              Start ────▶
TGACACTGGCATTGTTCATTATAGGAAACACGACTGCTGCTGATGATTATTCAG  324
 M  T  L  A  L  F  I  I  G  N  T  T  A  A  D  D  Y  S TTGTAGAGGAGCATGGGCAATTAAGTATTAGTAACGGAGAATTAGTCAATGATC  378
 V  V  E  E  H  G  Q  L  S  I  S  N  G  E  L  V  N  D XmnI
GAGGCGAACCAGTTCAGTTAAAAGGGATGAGTTCCCATGGTTTACAATGGTACG  432
 R  G  E  P  V  Q  L  K  G  M  S  S  H  G  L  Q  W  Y GTCAATTTGTAAACTATGAAAGCATGAAATGGCTAAGAGATGATTGGGGTATAA  486
 G  Q  F  V  N  Y  E  S  M  K  W  L  R  D  D  W  G  I CTGTATTCCGAGCAGCGATGTATACATCTTCGGGAGGATATATTGAGGATCCTT  540
 T  V  F  R  A  A  M  Y  T  S  S  G  G  Y  I  E  D  P CCGTAAAGGAAAAAGTAAAAGAGGCTGTTGAGGCTGCGATAGACCTTGGTATAT  594
 S  V  K  E  K  V  K  E  A  V  E  A  A  I  D  L  G  I ATGTCATAATTGATTGGCACATCCTTTCAGACAATGACCCGAATATATATAAAG  648
 Y  V  I  I  D  W  H  I  L  S  D  N  D  P  N  I  Y  K
```

FIG. 8

```
AAGAAGCAAAGGATTTCTTTGATGAAATGTCTGAGCTGTATGGAGATTACCCGA 702
 E   E   A   K   D   F   F   D   E   M   S   E   L   Y   G   D   Y   P

ATGTGATATACGAAATTGCAAATGAACCGAATGGTAGTGATGTTACGTGGGACA 756
 N   V   I   Y   E   I   A   N   E   P   N   G   S   D   V   T   W   D

Xmnl
ATCAAATAAAACCGTATGCAGAGGAAGTAATTCCGGTTATCCGTAACAATGATC 810
 N   Q   I   K   P   Y   A   E   E   V   I   P   V   I   R   N   N   D CTAATAACATTATTATTGTAGGTACAGGTACATGGAGTCAGGATGTTCATCATG 864
 P   N   N   I   I   I   V   G   T   G   T   W   S   Q   D   V   H   H CTGCTGATAATCAGTTAACAGATCCGAACGTCATGTATGCATTTCATTTTTATG 918
 A   A   D   N   Q   L   T   D   P   N   V   M   Y   A   F   H   F   Y CAGGAACACATGGACAAAATTTACGAGACCAAGTAGATTATGCATTAGATCAAG 972
 A   G   T   H   G   Q   N   L   R   D   Q   V   D   Y   A   L   D   Q GAGCAGCAATATTTGTTAGTGAATGGGGAACGAGTGAAGCTACTGGTGATGGCG 1026
 G   A   A   I   F   V   S   E   W   G   T   S   E   A   T   G   D   G GCGTGTTTTAGATGAAGCACAAGTGTGGATTGACTTTATGGATGAAAGAAATT 1080
 G   V   F   L   D   E   A   Q   V   W   I   D   F   M   D   E   R   N TAAGCTGGGCAAACTGGTCTCTAACGCACAAAGATGAGTCATCTGCGGCGTTAA 1134
 L   S   W   A   N   W   S   L   T   H   K   D   E   S   S   A   A   L TGCCAGGTGCAAGCCCAACTGGTGGGTGGACAGAGGCTGAACTATCTCCATCTG 1188
 M   P   G   A   S   P   T   G   G   W   T   E   A   E   L   S   P   S GGACATTTGTGAGGGAAAAAATAAGAGAGTCAGCAACAACACCACCTAGTGATC 1242
 G   T   F   V   R   E   K   I   R   E   S   A   T   T   P   P   S   D
```

FIG. 8A

```
CAACACCACCATCTGATCCAGATCCAGGTGAACCAGAACCAGATCCAGGTGAAC 1296
 P  T  P  P  S  D  P  D  P  G  E  P  E  P  D  P  G  E

CGGATCCAACGCCACCAAGTGATCCAGGAGATTATCCGGCATGGGATCCAAATA 1350
 P  D  P  T  P  P  S  D  P  G  D  Y  P  A  W  D  P  N

CAATTTATACAGATGAAATTGTGTACCATAACGGCCAGCTATGGCAAGCAAAAT 1404
 T  I  Y  T  D  E  I  V  Y  H  N  G  Q  L  W  Q  A  K

RsrII
GGTGGACGCAAAATCAAGAGCCAGGCGACCCATACGGTCCGTGGGAACCACTCA 1458
 W  W  T  Q  N  Q  E  P  G  D  P  Y  G  P  W  E  P  L

Mature End
AT TAA CGATATAATGATAGAAATTTACTAATGATATAAGGAGAATGCCAAGAGT 1512
 N  -

KpnI         SstI
CTAAATTGGACGATTGGCATTCTCATGGTACCTATTAGAGCTC
```

FIG. 8B

P300-CelB Fusion Construct #3

```
AvaI
CCCGGGACCTCTTTCCCTGCCAGGCTGAAGCGGTCTATTCATACTTTCGAACTG 54

AACATTTTTCTAAAACAGTTATTAATAACCAAAAAATTTTAAATTGGTCCTCCA 108
                                              mRNA Start
      StuI                                      →
AAAAAATAGGCCTACCATATAATTCATTTTTTTCTATAATAAATTAACAGAAT 162

RBS
AATTGGAATAGATTATATTATCCTTCTATTTAAATTATTCTGAATAAAGAGGAG 216
         Signal Sequence Start
              →
GAGAGTGAGTAATGATGAGGAAAAAGAGTTTTTGGCTTGGGATGCTGACGGCCT 270
            M  M  R  K  K  S  F  W  L  G  M  L  T  A
                                          Mature Sequence
                              PstI        Start →
TCATGCTCGTGTTCACGATGGCATTCAGCGATTCCGCTTCTGCAGATGATTATT 324
 F  M  L  V  F  T  M  A  F  S  D  S  A  S  A  D  D  Y CAGTTGTAGAGGAGCATGGGCAATTAAGTATTAGTAACGGAGAATTAGTCAATG 378
 S  V  V  E  E  H  G  Q  L  S  I  S  N  G  E  L  V  N XmnI
ATCGAGGCGAACCAGTTCAGTTAAAAGGGATGAGTTCCCATGGTTTACAATGGT 432
 D  R  G  E  P  V  Q  L  K  G  M  S  S  H  G  L  Q  W ACGGTCAATTTGTAAACTATGAAAGCATGAAATGGCTAAGAGATGATTGGGGTA 486
 Y  G  Q  F  V  N  Y  E  S  M  K  W  L  R  D  D  W  G TAACTGTATTCCGAGCAGCGATGTATACATCTTCGGGAGGATATATTGAGGATC 540
 I  T  V  F  R  A  A  M  Y  T  S  S  G  G  Y  I  E  D CTTCCGTAAAGGAAAAAGTAAAAGAGGCTGTTGAGGCTGCGATAGACCTTGGTA 594
 P  S  V  K  E  K  V  K  E  A  V  E  A  A  I  D  L  G TATATGTCATAATTGATTGGCACATCCTTTCAGACAATGACCCGAATATATATA 648
 I  Y  V  I  I  D  W  H  I  L  S  D  N  D  P  N  I  Y
```

FIG. 9

```
AAGAAGAAGCAAAGGATTTCTTTGATGAAATGTCTGAGCTGTATGGAGATTACC  702
 K   E   E   A   K   D   F   F   D   E   M   S   E   L   Y   G   D   Y

CGAATGTGATATACGAAATTGCAAATGAACCGAATGGTAGTGATGTTACGTGGG  756
 P   N   V   I   Y   E   I   A   N   E   P   N   G   S   D   V   T   W

XmnI
ACAATCAAATAAAACCGTATGCAGAGGAAGTAATTCCGGTTATCCGTAACAATG  810
 D   N   Q   I   K   P   Y   A   E   E   V   I   P   V   I   R   N   N

ATCCTAATAACATTATTATTGTAGGTACAGGTACATGGAGTCAGGATGTTCATC  864
 D   P   N   N   I   I   I   V   G   T   G   T   W   S   Q   D   V   H

ATGCTGCTGATAATCAGTTAACAGATCCGAACGTCATGTATGCATTTCATTTTT  918
 H   A   A   D   N   Q   L   T   D   P   N   V   M   Y   A   F   H   F

ATGCAGGAACACATGGACAAAATTTACGAGACCAAGTAGATTATGCATTAGATC  972
 Y   A   G   T   H   G   Q   N   L   R   D   Q   V   D   Y   A   L   D

AAGGAGCAGCAATATTTGTTAGTGAATGGGGAACGAGTGAAGCTACTGGTGATG  1026
 Q   G   A   A   I   F   V   S   E   W   G   T   S   E   A   T   G   D

GCGGCGTGTTTTTAGATGAAGCACAAGTGTGGATTGACTTTATGGATGAAAGAA  1080
 G   G   V   F   L   D   E   A   Q   V   W   I   D   F   M   D   E   R

ATTTAAGCTGGGCAAACTGGTCTCTAACGCACAAAGATGAGTCATCTGCGGCGT  1134
 N   L   S   W   A   N   W   S   L   T   H   K   D   E   S   S   A   A

TAATGCCAGGTGCAAGCCCAACTGGTGGGTGGACAGAGGCTGAACTATCTCCAT  1188
 L   M   P   G   A   S   P   T   G   G   W   T   E   A   E   L   S   P

CTGGGACATTTGTGAGGGAAAAAATAAGAGAGTCAGCAACAACACCACCTAGTG  1242
 S   G   T   F   V   R   E   K   I   R   E   S   A   T   T   P   P   S

ATCCAACACCACCATCTGATCCAGATCCAGGTGAACCAGAACCAGATCCAGGTG  1296
 D   P   T   P   P   S   D   P   D   P   G   E   P   E   P   D   P   G
```

FIG. 9A

```
AACCGGATCCAACGCCACCAAGTGATCCAGGAGATTATCCGGCATGGGATCCAA 1350
 E   P  D  P  T  P  P  S  D  P  G  D  Y  P  A  W  D  P

ATACAATTTATACAGATGAAATTGTGTACCATAACGGCCAGCTATGGCAAGCAA 1404
 N  T  I  Y  T  D  E  I  V  Y  H  N  G  Q  L  W  Q  A

RsrII
AATGGTGGACGCAAAATCAAGAGCCAGGCGACCCATACGGTCCGTGGGAACCAC 1458
 K  W  W  T  Q  N  Q  E  P  G  D  P  Y  G  P  W  E  P

Mature End
TCAATTAACGATATAATGATAGAAATTTACTAATGATATAAGGAGAATGCCAAG 1512
 L  N  -

KpnI       SstI
AGTCTAAATTGGACGATTGGCATTCTCATGGTACCTATTAGAGCTC
```

FIG. 9B

P300-CelB Fusion Construct #4

```
AvaI
CTCGGGACCTCTTTCCCTGCCAGGCTGAAGCGGTCTATTCATACTTTCGAACTG  54

AACATTTTTCTAAAACAGTTATTAATAACCAAAAAATTTTAAATTGGTCCTCCA  108
                                                mRNA Start
        StuI                                       →
AAAAAATAGGCCTACCATATAATTCATTTTTTTCTATAATAAATTAACAGAAT  162
                                                Signal Sequence
                            RBS                  Start →
AATTGGATCCTTCTATTTAAATTATTCTGAATAAAGAGGAGAGAGTGAGTAAT  216
                                                       M GATGAGGAAAAGAGTTTTTGGCTTGGGATGCTGACGGCCTTCATGCTCGTGTT  270
 M  R  K  K  S  F  W  L  G  M  L  T  A  F  M  L  V  F Mature Sequence Start
        ClaI         PstI →
CACGATGGCATCGATCGCATCGGCTGCAGATGATTATTCAGTTGTAGAGGAGCA  324
 T  M  A  S  I  A  S  A  A  D  D  Y  S  V  V  E  E  H XmnI
TGGGCAATTAAGTATTAGTAACGGAGAATTAGTCAATGATCGAGGCGAACCAGT  378
 G  Q  L  S  I  S  N  G  E  L  V  N  D  R  G  E  P  V TCAGTTAAAAGGGATGAGTTCCCATGGTTTACAATGGTACGGTCAATTTGTAAA  432
 Q  L  K  G  M  S  S  H  G  L  Q  W  Y  G  Q  F  V  N CTATGAAAGCATGAAATGGCTAAGAGATGATTGGGGTATAACTGTATTCCGAGC  486
 Y  E  S  M  K  W  L  R  D  D  W  G  I  T  V  F  R  A AGCGATGTATACATCTTCGGGAGGATATATTGAGGATCCTTCCGTAAAGGAAAA  540
 A  M  Y  T  S  S  G  G  Y  I  E  D  P  S  V  K  E  K AGTAAAAGAGGCTGTTGAGGCTGCGATAGACCTTGGTATATATGTCATAATTGA  594
 V  K  E  A  V  E  A  A  I  D  L  G  I  Y  V  I  I  D TTGGCACATCCTTTCAGACAATGACCCGAATATATATAAAGAAGAAGCAAAGGA  648
 W  H  I  L  S  D  N  D  P  N  I  Y  K  E  E  A  K  D
```

FIG. 10

```
TTTCTTTGATGAAATGTCTGAGCTGTATGGAGATTACCCGAATGTGATATACGA 702
 F   F   D   E   M   S   E   L   Y   G   D   Y   P   N   V   I   Y   E

AATTGCAAATGAACCGAATGGTAGTGATGTTACGTGGGACAATCAAATAAAACC 756
 I   A   N   E   P   N   G   S   D   V   T   W   D   N   Q   I   K   P

XmnI
GTATGCAGAGGAAGTAATTCCGGTTATCCGTAACAATGATCCTAATAACATTAT 810
 Y   A   E   E   V   I   P   V   I   R   N   N   D   P   N   N   I   I

TATTGTAGGTACAGGTACATGGAGTCAGGATGTTCATCATGCTGCTGATAATCA 864
 I   V   G   T   G   T   W   S   Q   D   V   H   H   A   A   D   N   Q

GTTAACAGATCCGAACGTCATGTATGCATTTCATTTTTATGCAGGAACACATGG 918
 L   T   D   P   N   V   M   Y   A   F   H   F   Y   A   G   T   H   G

ACAAAATTTACGAGACCAAGTAGATTATGCATTAGATCAAGGAGCAGCAATATT 972
 Q   N   L   R   D   Q   V   D   Y   A   L   D   Q   G   A   A   I   F

TGTTAGTGAATGGGGAACGAGTGAAGCTACTGGTGATGGCGGCGTGTTTTTAGA 1026
 V   S   E   W   G   T   S   E   A   T   G   D   G   G   V   F   L   D

TGAAGCACAAGTGTGGATTGACTTTATGGATGAAAGAAATTTAAGCTGGGCAAA 1080
 E   A   Q   V   W   I   D   F   M   D   E   R   N   L   S   W   A   N

CTGGTCTCTAACGCACAAAGATGAGTCATCTGCGGCGTTAATGCCAGGTGCAAG 1134
 W   S   L   T   H   K   D   E   S   S   A   A   L   M   P   G   A   S

CCCAACTGGTGGGTGGACAGAGGCTGAACTATCTCCATCTGGGACATTTGTGAG 1188
 P   T   G   G   W   T   E   A   E   L   S   P   S   G   T   F   V   R

GGAAAAAATAAGAGAGTCAGCAACAACACCACCTAGTGATCCAACACCACCATC 1242
 E   K   I   R   E   S   A   T   T   P   P   S   D   P   T   P   P   S
```

FIG. 10A

```
TGATCCAGATCCAGGTGAACCAGAACCAGATCCAGGTGAACCGGATCCAACGCC   1296
  D   P   D   P   G   E   P   E   P   D   P   G   E   P   D   P   T   P

ACCAAGTGATCCAGGAGATTATCCGGCATGGGATCCAAATACAATTTATACAGA   1350
  P   S   D   P   G   D   Y   P   A   W   D   P   N   T   I   Y   T   D

TGAAATTGTGTACCATAACGGCCAGCTATGGCAAGCAAAATGGTGGACGCAAAA   1404
  E   I   V   Y   H   N   G   Q   L   W   Q   A   K   W   W   T   Q   N

RsrII                    Mature End
TCAAGAGCCAGGCGACCCATACGGTCCGTGGGAACCACTCAATTAACGATATAA   1458
  Q   E   P   G   D   P   Y   G   P   W   E   P   L   N   -

TGATAGAAATTTACTAATGATATAAGGAGAATGCCAAGAGTCTAAATTGGACGA   1512

KpnI        SstI
TTGGCATTCTCATGGTACCTATTAGAGCTC
```

FIG. 10B

EXPRESSION SYSTEMS FOR COMMERCIAL PRODUCTION OF CELLULASE AND XYLANASE IN *BACILLUS SUBTILIS* AND *BACILLUS LICHENIFORMIS*

BENEFIT OF EARLIER FILING DATE UNDER 35 U.S.C. §119(e)

This application claims the benefit of earlier filed and copending provisional application serial number 60/002,106, filed on Aug. 10, 1995.

BACKGROUND OF THE INVENTION

FIELD OF THE INVENTION

This invention relates to the enhanced production of cellulases by Bacillus sp. More specifically, the invention relates to *Bacillus subtilis* and *Bacillus licheniformis* transformed with genetic constructs containing a *Bacillus licheniformis* ATCC 53926 protease promoter and signal sequence to express alkalophilic cellulase genes.

SUMMARY OF THE INVENTION

It has been discovered that increased production of a heterologous cellulase can be achieved in a Bacillus host by using an expression system composed of either a native or modified P300 promoter, ribosomal binding site, initiation codon and signal sequence.

BRIEF DESCRIPTION OF THE DRAWINGS

FIG. 7 (SEQ ID NO:1) is the DNA sequence of the P300-CelB fusion construct #1.

FIG. 8 (SEQ ID NO:2) is the DNA sequence of the P300-CelB fusion construct #2.

FIG. 9 (SEQ ID NO:3) is the DNA sequence of the P300-CelB fusion construct #3.

FIG. 10 (SEQ ID NO:4) is the DNA sequence of the P300-CelB fusion construct #4.

DESCRIPTION OF THE PREFERRED EMBODIMENTS

Other than in the claims and in the operating examples, or where otherwise indicated, all numbers expressing quantities of ingredients or reaction conditions used herein are to be understood as modified in all instances by the term "about".

The term P300, as used in this specification, is synonymous with *B. licheniformis* ATCC 53926. The P300 strain and the Bacillus lentus alkaline protease (BLAP) gene are described in U.S. Pat. No. 5,352,604, the entire contents of which are incorporated herein by reference.

The present invention uses a *Bacillus licheniformis* ATCC 53926 protease promoter and signal sequence to express alkalophilic cellulase genes within species of Bacillus.

Figure 1:
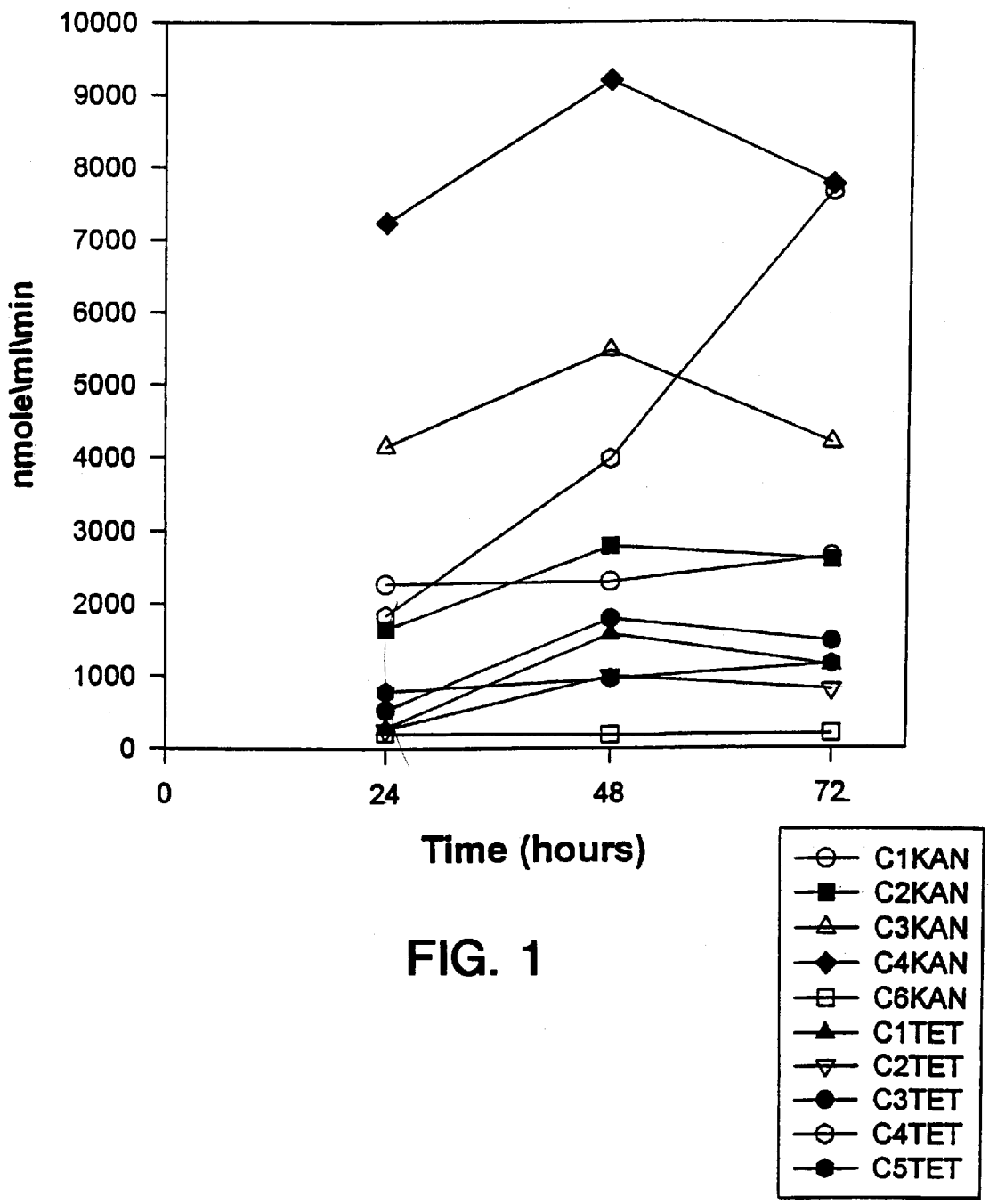
FIG. 1 shows a comparison of cellulase production in MLBSP medium for all the constructs according to the invention.
Figure 2:
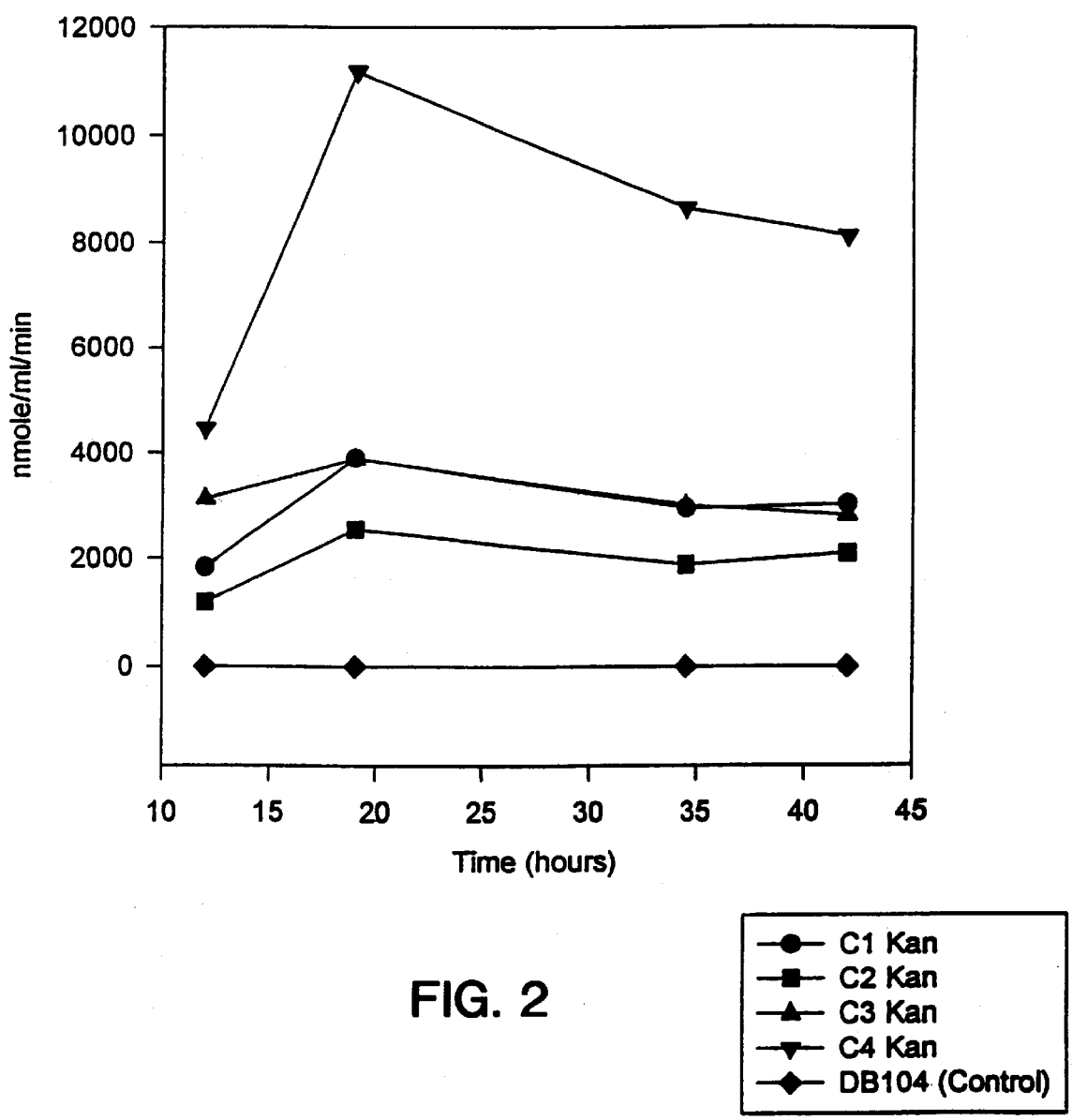
FIGS. 2 and 3 show a comparison of cellulase production in the C1 through C4 KAN constructs in *B. subtilis* grown in MLBSP and 2XYT media.
Figure 3:
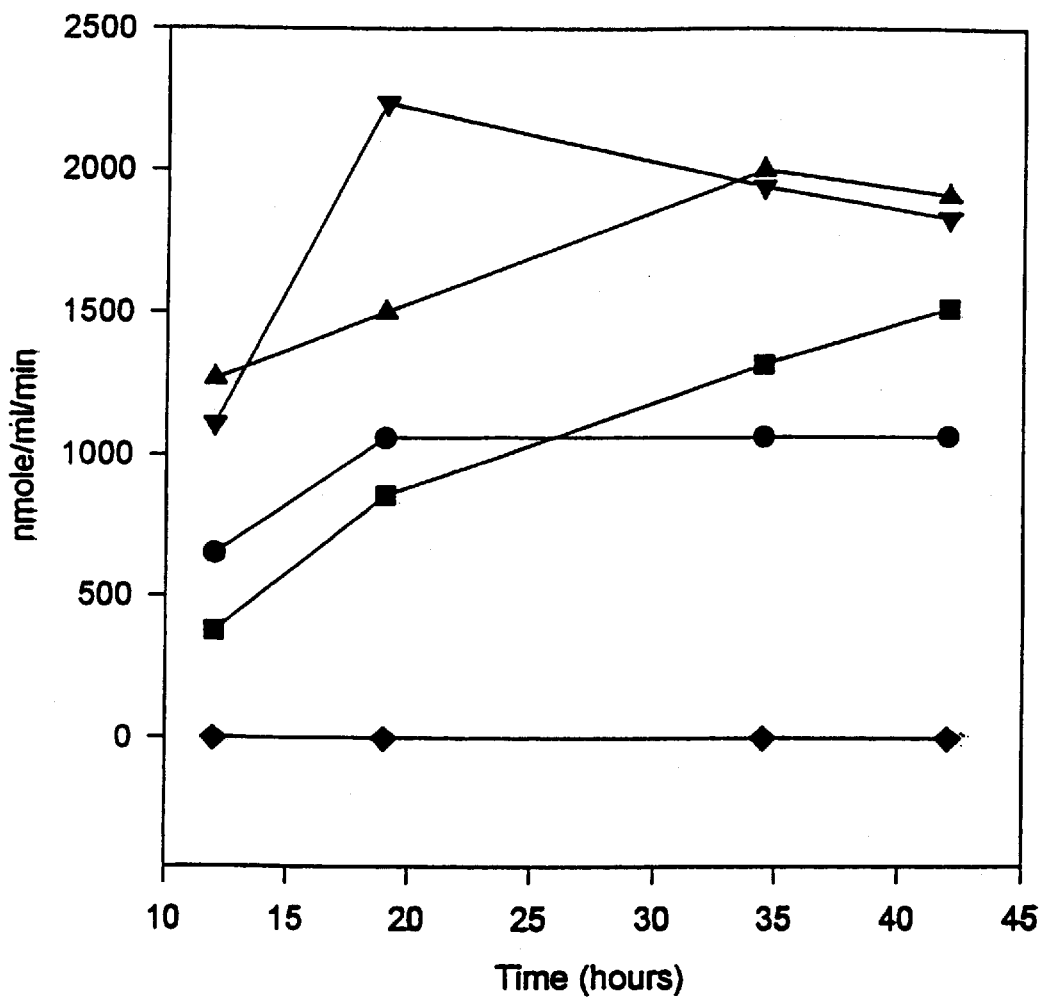
Figure 4:
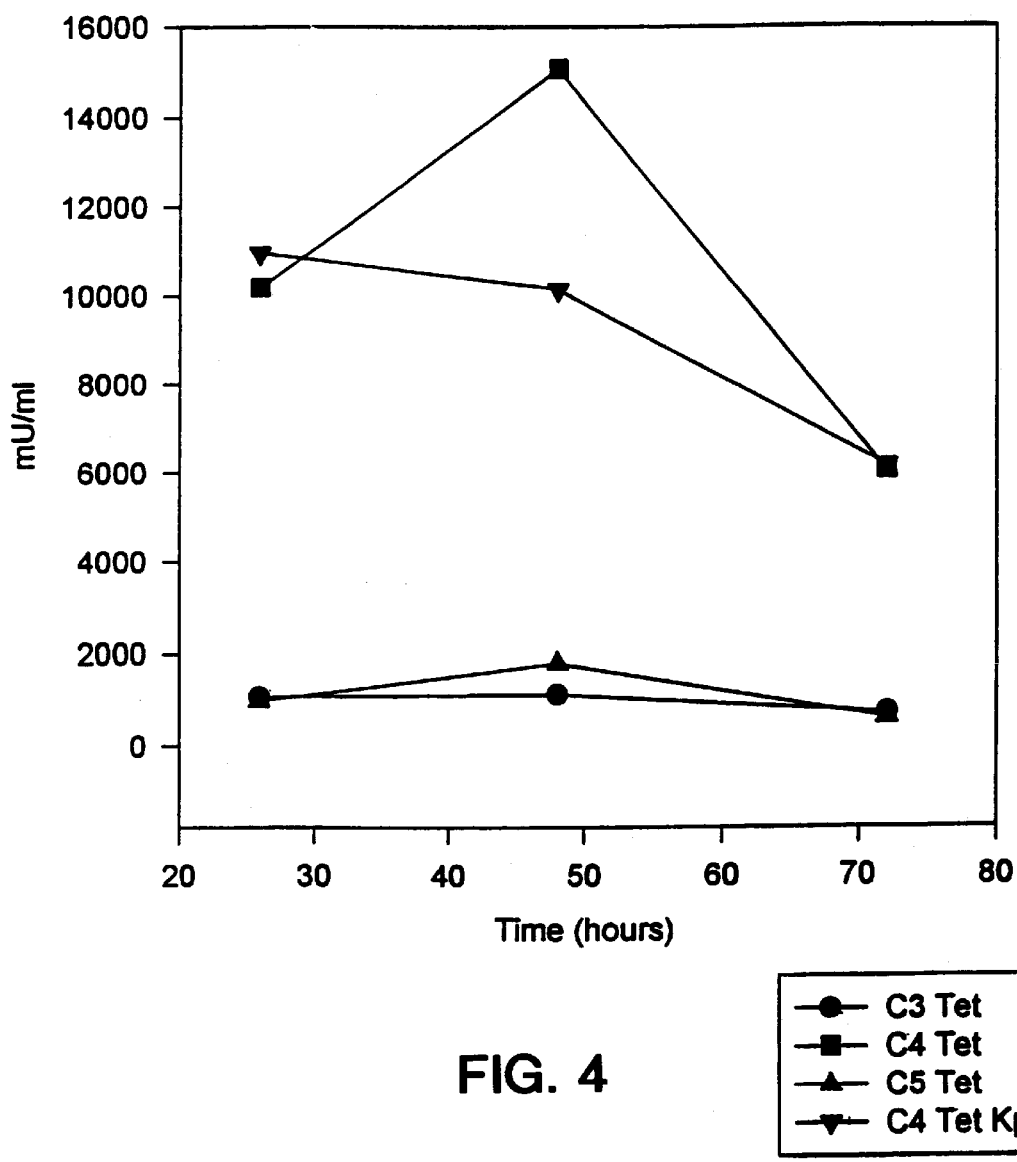
FIGS. 4 and 5 show that the C4TET construct produced much more cellulase than the other constructs.
Figure 5:
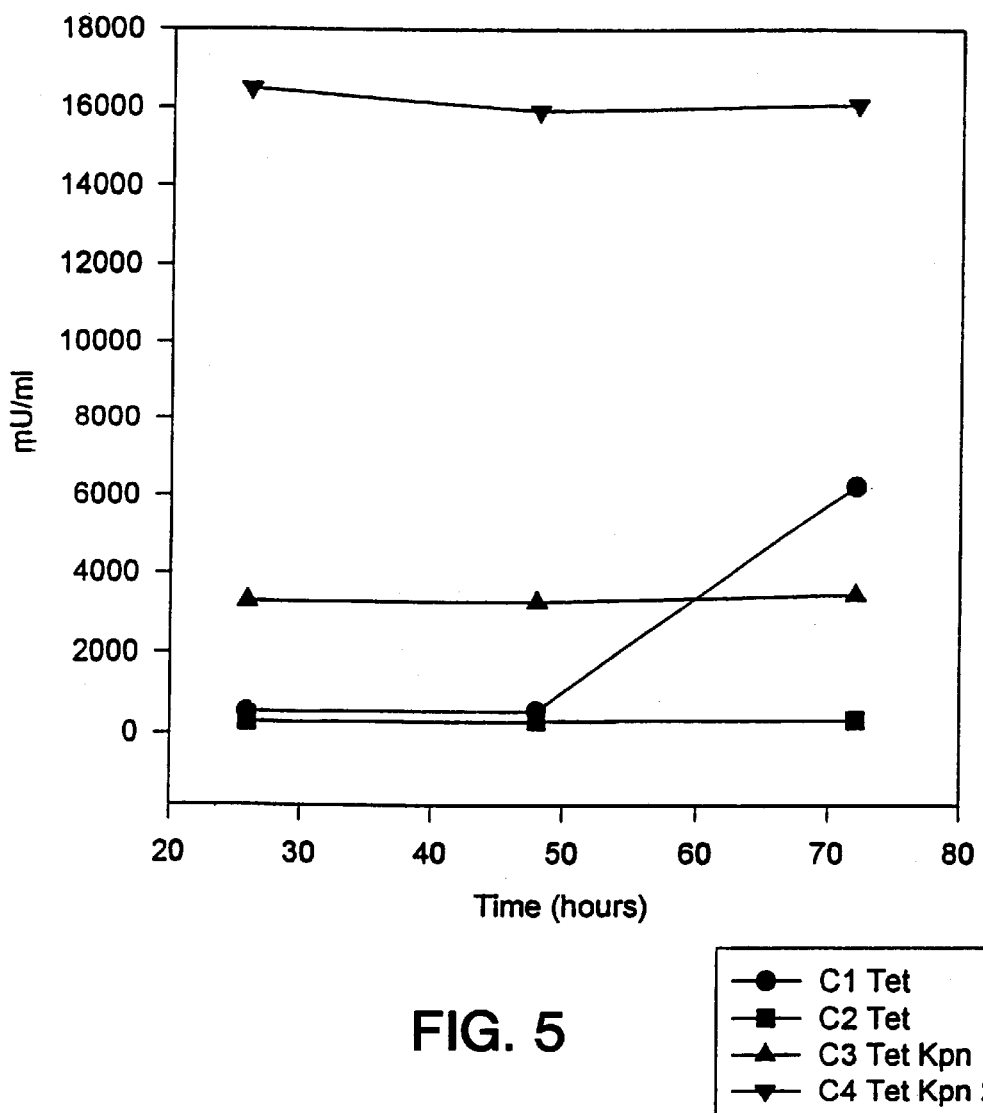
Figure 6:
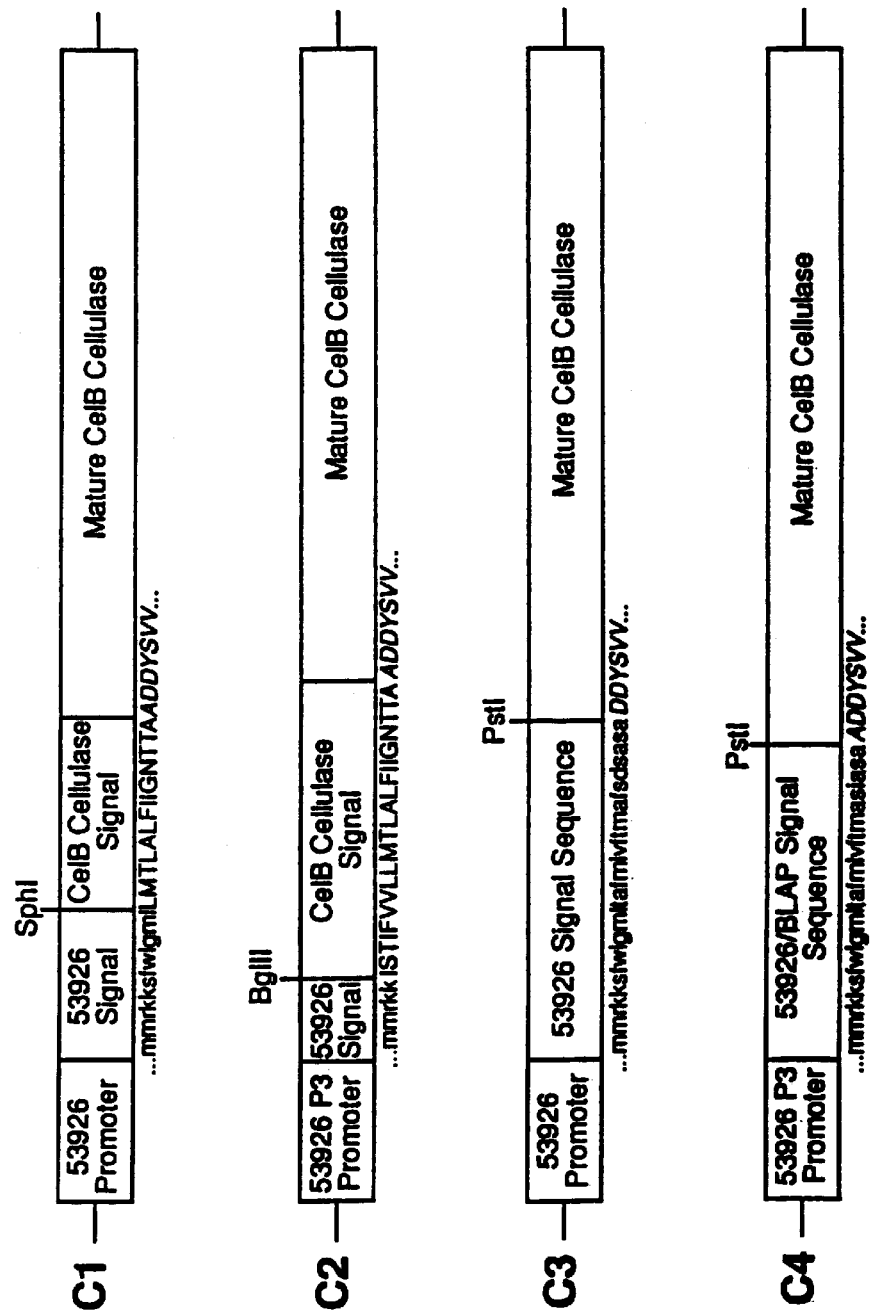
FIG. 6 is a depiction of the ATCC 53962 protease and CelB cellulase gene fusions.

Increased production of a heterologous cellulase can be achieved in a Bacillus host by using an expression system composed of either a native or modified P300 promoter, ribosomal binding site, initiation codon and signal sequence. A principal advantage of this invention is the enhanced production of cellulases by Bacillus sp. in both shake flasks, pilot scale fermenters, and large scale commercial fermentations. In addition to cellulase yield increases, which are much greater than the yields associated with the native cellulase gene and its controlling elements, the production of the cellulase also occurs at earlier times in the fermentation process. The improvements for cellulase production in both *Bacillus subtilis* and *Bacillus licheniformis* are shown in FIGS. (1 through 5) which compare cellulase production in shake flasks using two typical growth media's, either 2XYT or MLBSP. Any suitable fermentation medium can be used to grow the transformed organisms described herein. FIG. 1 shows a comparison of cellulase production in MLBSP medium for all the constructs. As can be seen from these results, variable but increased cellulase yields were observed for all but one construct (C2TET), as compared to the native CelB cellulase gene present in C5TET and C6KAN. FIGS. 2 and 3 compare cellulase production in the C1 through C4 KAN constructs in *B. subtilis* grown in MLBSP and 2XYT media. In both MLBSP and 2XYT the C4 and C3 constructs produced the highest yields of cellulase. Some of the better constructs demonstrated a ten to forty fold increase in cellulase yields as compared to the *Bacillus subtilis* DB104 control host strain with the native CelB gene cloned into either C5TET or C6KAN. As shown in FIGS. 2 and 3, the *B. subtilis* DB104 host strain did not produce detectable cellulase at any assay time during the experiment. Only the TET versions of the constructs were tested for cellulase production in *Bacillus licheniformis*. The experimental results in FIGS. 4 and 5 show that the C4TET construct produced much more cellulase than the other constructs and a 7 to 8-fold in cellulase relative to the native CelB gene present in construct C5TET. These results clearly show the increased production of a heterologous cellulase which can be achieved in a Bacillus host by using an expression system composed of either a native or modified P300 promoter, ribosomal binding site, initiation codon and signal sequence.

Strategies to Clone and Over Express the CelB Alkaline Cellulase Gene from Bacillus SP. N4 (ATCC 21833)

1. Construct #1: Hybrid signal between P300 and CelB cellulase
   A. Introduce a Sphl site in pMc13C between the Aval and Nhel sites (within the P300 signal sequence) using site-directed mutagenesis. The PCR fragment carrying the new Sphl site will be cloned back into pMc13C as an Aval/Nhel fragment. This new plasmid will be labeled pMc13Sph.
   B. Amplify partial CelB signal and mature sequences as a Sphl/Sstl fragment using PCR.
   C. Prepare pMc13Sphl DNA, digest plasmid with Sphl and Sstl, and purify the large fragment (vector) using HPLC.
   D. Clone fragment from (B) into vector in © as a Sphl/Sstl fragment, and transform into *E. coli* WK6. This new clone will be labeled P300NK2C1.
   E. Prepare P300NK2C1 DNA, digest plasmid with Aval/Sstl, and purify the small fragment (insert) which contains the P300-CelB fusion using HPLC.
   F. Prepare pC51 and pH70 DNAs, digest each plasmid with Aval and Sstl, and purify the large fragment (vector) from each plasmid using HPLC.

G. Clone the P300-CelB fusion from (E) into the vectors from (F). The Tc construct will be labeled C1TET and the Km construct C1KAN. Transform C1TET and C1KAN into *B. subtilis* DB104 and *B. licheniformis* ATCC 53926.

2. Construct #2: Hybrid signal between P300 and CelB cellulase (includes most of the CelB cellulase signal sequence)

A. Introduce a Bglll site in pMc13C between the Aval and Nhel sites (within the P300 signal sequence) using site-directed mutagenesis. The PCR fragment carrying the new Bglll site will be cloned back into pMc13C as an Aval/Nhel fragment. This new plasmid will be labeled pMc13Bgl.

B. Amplify partial CelB signal and mature sequences as a Bglll/Sstl fragment using PCR.

C. Prepare pMc13Bgl DNA, digest plasmid with Bglll and Sstl, and purify the large fragment (vector) using HPLC.

D. Clone fragment from (B) into vector in © as a Bglll/Sstl fragment, and transform into *E coli* WK6. The new clone will be labeled P300NK2C2.

E. Prepare P300NK2C2 DNA, digest plasmid with Aval and Sstl, and purify the small fragment (insert) which contains the P300-CelB fusion using HPLC.

F. Prepare pC51 and pH70 DNAs, digest each plasmid with Aval and Sstl and purify the large fragment (vector) from each plasmid using HPLC.

G. Clone the P300-CelB fusion from (E) into the vectors from (F). The Tc construct will be labeled C2TET and the Km construct C2KAN.

Transform C1TET and C1KAN into *B. subtilis* DB104 and *B. licheniformis* ATCC 53926.

3. Construct #3: Hybrid between P300 signal and CelB mature cellulase sequences

A. Introduce a Pstl site at the end of the P300 pre region in pC51 between the Aval and Hindlll sites using site-directed mutagenesis. The PCR fragment carrying the new Pstl site will be cloned back into pC51 as an Aval/Hindlll fragment. This new plasmid will be labeled pC51 Pst.

B. Amplify the CelB mature cellulase as a Pstl/Sstl fragment using PCR.

C. Prepare pC51 Pst DNA, digest plasmid with Pstl and Sstl and purify the large fragment (vector) using HPLC.

D. Clone fragment from (B) into vector in © as a Pstl/Sstl fragment and transform into *B. subtilis* DB104 and *B. licheniformis* ATCC 53926. This new construct will be labeled C3TET.

E. Prepare pH70 and C3TET DNAs and digest each plasmid with Aval and Sstl. Purify the large fragment (vector) from pH70 and the small fragment (insert) from C3TET using HPLC.

F. Clone the insert from (E) into the vector, and transform into *B. subtilis* DB104 and *B. licheniformis* ATCC 53926. This construct will be labeled C3KAN.

4. Construct #4: Hybrid between the P300 BLAP Cla Fusion signal and the CelB mature cellulase sequence A. Introduce a Pstl site at the end of the P300 pre region of pCB56P3 between the Aval and Nhel sites using site-directed mutagenesis. The PCR fragment carrying the new Pstl site will be cloned back into pC51 as an Aval/Nhel fragment. This new plasmid will be labeled 56P3Pst.

B. Prepare 56P3Pst DNA, digest plasmid with Pstl and Sstl and purify the large fragment (vector) using HPLC.

C. Clone the CelB mature cellulase amplified as a Pstl/Sstl from (3B) into vector in (B) as a Pstl/Sstl fragment, and transform into *B. subtilis* DB104 and *B. licheniformis* ATCC 53926. This new construct will be labeled C4TET.

D. Prepare C4TET and pH70 DNAs and digest each plasmid with Aval and Sstl. Purify the small fragment (insert) from C4TET and the large fragment (vector) from pH70 using HPLC.

E. Clone the insert from (D) into the vector, and transform into *B. subtilis* DB104 and *B. licheniformis* ATCC 53926. This new construct will be labeled C4KAN.

5. Construct 5: Cloning of the entire CelB cellulase gene into pBC16 as a Sphl/Xbal fragment A. Prepare pBC16 DNA, digest plasmid with Sphl and Xbal, and purify the large fragment (vector) using HPLC.

B. Amplify the entire CelB cellulase gene as a Sphl/Xbal fragment using PCR (insert).

C. Clone the amplified fragment in (B) into vector in (A) in the counter clockwise direction and transform into *B. subtilis* DB104 and *B. licheniformis* ATCC 53926. This construct will be labeled C5TET.

6. Construct #6: Cloning of the entire pNK2 cellulase gene into PUB 110 as a Sphl/Xbal fragment A. Prepare pUB110 DNA, digest plasmid with Sphl and Xbal, and purify the large fragment (vector) using HPLC.

B. Clone the amplified fragment in (5B) into vector in (A) in the counter clockwise direction, and transform into *B. subtilis* DB104 and *B. licheniformis* ATCC 53926. This construct will be labeled C6KAN.

EXAMPLE 1

1. The pNK2 alkaline cellulase gene was cloned into plasmid pTZ18R as a EcoRl/Hindlll fragment and transformed into *E. coli* BCE101. This new clone was labeled pCelBN4 (as received from Duesseldorf). The pNK2 alkaline cellulase gene is referred in the literature as the CelB gene from Bacillus sp. N4 (ATCC #21833).

2. REFERENCE "Nucleotide Sequence of Two Cellulase Genes from Alkalophilic Bacillus sp. Strain N-4 and Their Strong Homology" Fukumori, et. al. (1986) Journal of Bacteriology, Nov., p. 479–485.

3. The nucleotide and amino acid sequences for all constructs will be copied into notebook #7557.

Media for Production of Cellulase

1. Composition of MLBSP Medium

| Component | Quantity (for 1 liter of media) |
| --- | --- |
| deionized water | 750 ml |
| Difco Casitone | 10 gm |
| Difco Tryptone | 20 gm |
| Difco Yeast Extract | 10 gm |
| NaCl | 5 gm |
| Na-Succinate | 27 gm |

Adjust media to pH 7.2 by addition of NaOH, and the volume to 815 ml with water. Autoclave at 121° C., 15 psi for 15 min. Cool media before addition of the following sterile stock solutions:

| Component | | Quantity (for 1 liter of media) |
|---|---|---|
| $MgSO_4.7H_2O$ | (100 mg/ml stock, autoclaved) | 1 ml |
| $CaCl_2.2H_2O$ | (30 mg/ml stock, autoclaved) | 2.5 ml |
| $MnCl_2.2H_2O$ | (1 mM stock, autoclaved) | 0.5 ml |
| $FeSO_4.7H_2O$ | (1 mM stock, filter sterilized) | 0.5 ml |
| Glucose | (25% (w/v) stock, autoclaved) | 80 ml |
| PIPES Buffer[1] | (pH 7.2, 1 M stock, autoclaved) | 50 ml |
| $KPO_4$ Buffer[2] | (pH 7.0, 1.5 M stock, autoclaved) | 50 ml |

[1]Piperazine-N,N'bis(2-ethane sulfonic acid).
[2]A suffcient amount of 1.5 M dibasic phosphate ($K_2HPO_4$) was added to 200 ml of 1.5 M monobasic phosphate ($KH_2PO_4$) to adjust pH to 6.0. The final pH was adjusted to 7.0 with 4 M KOH.

Either kanamycin or tetracycline antibiotic stock solutions were added to the media just before use to a final concentration of 20 μg/ml and 15 μg/ml respectively.

2. 2X YT Medium 1.6% Difco Bactopeptone 1.0% Yeast Extract 0.5% NaCl

EXAMPLE 2

Shake Flask Procedure for Evaluating Cellulase Production

Inoculate preculture flasks containing 40 ml Luria Broth with *Bacillus subtilis* DB104, and the following pUB110 Kanamycin resistant *Bacillus subtilis* DB104 constructs: C1 Kan, C2 Kan, C3 Kan, C4 Kan. Add Kanamycin at 20 μg/ml to all flasks except DB104 containing flask. Incubate all flasks at 37° C., 250 RPM for 9 hours on a bench top shaker.

Inoculate duplicate shake flasks containing MLBSP (without glucose) and 2 x YT media for each culture. Use a 5% inoculation into 100 ml of each media with 20 μg Kanamycin (except for DB104) in 500 ml baffled shake flasks. Place flasks on a floor shaker at 37° C., 250 RPM. Remove 7 ml samples from each shake flask at 12, 19, 34.5 and 42 hours. Centrifuge samples at 12,000 RPM in an SA-600 rotor for 10 min to separate cells from supernatant. Pour off supernatant into Coming centrifuge tubes and store at 4° C. until ready to assay for cellulase.

EXAMPLE 3

Reagents 0.5M NaOH:

Dissolve 20.0 g NAOH into distilled $H_2O$ to a final volume of 1 L.

50 mM Glycine Buffer pH=9.0

3.75 g Glycine 800 ml distilled $H_2O$ adjust with 2M NaOH to pH=9.0

Add to 1 L with distilled $H_2O$

1% PABAH Solution (containing 1 mM Bismuth) in NaOH 1 g PABAH 100 ml 0.5M NaOH

100 μl bismuth stock solution

Substrate Solution 2.5% Carboxymethylcellulose (CMC) pH=9.0

2.5 g Carboxymethylcellulose (low viscosity)

dissolve in a final volume of 100 ml Glycine buffer pH=9.0

Bismuth Stock Solution

1M Bismuth-nitrate

1M Ka-Na-tartrate

3M NaOH dissolve in a final volume of 100 ml distilled $H_2O$

Enzyme Solution

Dilute supernatant samples taken from shake flask experiment as necessary in 50 mM Glycine buffer pH 9.0.

Procedure

Add 250 μl 2.5% CMC substrate solution to 2.2 ml capped test tubes using a positive displacement pipet. Add 250 μl enzyme solution to test tube containing CMC substrate solution and vortex to mix. Assay triplicate samples of enzyme solution. Prepare an additional test tube containing 250 μl 2.5% CMC solution to use as a blank for each set of triplicate samples. Incubate all tubes at 40° C. in a water bath for 30 min. Remove test tubes from water bath and add 500 μl 1% PAHBAH solution to each sample containing enzyme solution and to blanks. Add 250 μl enzyme solution to each blank. Incubate all test tubes in a water bath at 70° C. for 10 min. Place tubes in a water bath at 10°–15° C. for 1–2 min to cool. Read samples on spectrophotometer at 410 nm immediately.

Calculation

To calculate nmol/ml/min glucose released in assay use the following formula: difference in absorption (ave sample absorbance-blank)* assay volume * dilution factor 0.065 ml/nmol * 0.25 ml * 30 min

Deposit of Microorganisms

A living culture of plasmid C4TEt in *Bacillus subtilis*, assigned the ATCC Designation 69878, has been accepted for Deposit under the Budapest Treaty on the International Recognition of the Deposit of Microorganisms for the purposes of patent procedure by the American Type Culture Collection, 12301 Parklawn Drive, Rockville, Md. 20852.

What is claimed is:

1. A C1 expression system, composed of a DNA sequence comprising in the direction of transcription, a promoter element, a ribosomal binding site, an initiation codon and the first twelve amino acids of the signal sequence of the *Bacillus licheniformis* ATCC 53926 alkaline protease gene operably linked to a DNA sequence encoding approximately fourteen amino acids of the signal sequence and all of the mature sequence of a cellulase enzyme.

2. A C2 expression system, composed of a DNA sequence comprising in the direction of transcription, a promoter element, a ribosomal binding site, an initiation codon and the first five amino acids of the *Bacillus licheniformis* ATCC 53926 alkaline protease gene operably linked to a DNA sequence encoding both the signal sequence and the mature sequence of a cellulase enzyme.

3. A C4 expression system, composed of a DNA sequence comprising in the direction of transcription, a modified ATCC 53926 alkaline protease promoter element, a ribosomal binding site, an initiation codon and the first twenty-one amino acids of the signal sequence of the *Bacillus licheniformis* ATCC 53926 alkaline protease gene operably linked to a DNA sequence encoding the last five amino acids of the BLAP signal sequence and all of the mature sequence of a cellulase enzyme.

4. A C5 or C6 expression system, composed of a DNA sequence comprising in the direction of transcription, a promoter element, a ribosomal binding site, an initiation codon of the *Bacillus licheniformis* ATCC 53926 alkaline protease gene operably linked to a DNA sequence encoding all of the signal sequence and the mature sequence of a cellulase enzyme.

5. Plasmids capable of replicating in Bacillus sp. which carry the expression system described in claim 1.

6. Plasmids capable of replicating in Bacillus sp. which carry the expression system described in claim 2.

7. Plasmids capable of replicating in Bacillus sp. which carry the expression system described in claim 3.

8. Plasmids capable of replicating in Bacillus sp. which carry the expression system described in claim 4.

9. A transformed Bacillus host comprising a plasmid carrying an expression system described in claim 1.

10. A transformed Bacillus host comprising a plasmid carrying an expression system described in claim 2.

11. A transformed Bacillus host comprising a plasmid carrying an expression system described in claim 3.

12. A transformed Bacillus host comprising a plasmid carrying an expression system described in claim 4.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

( A ) LENGTH: 1552 base pairs ( B ) TYPE: nucleic acid ( C ) STRANDEDNESS: double (D) TOPOLOGY: linear (ii) MOLECULE TYPE: other nucleic acid
    (A) DESCRIPTION: /desc = "Bacterial DNA"

(vii) IMMEDIATE SOURCE:
    (B) CLONE: P300CELB Fusion Construct #1

(xi) SEQUENCE DESCRIPTION: SEQ ID NO:1:

| | | | | | | |
|---|---|---|---|---|---|---|
| CTCGGGACCT | CTTTCCCTGC | CAGGCTGAAG | CGGTCTATTC | ATACTTTCGA | ACTGAACATT | 60 |
| TTTCTAAAAC | AGTTATTAAT | AACCAAAAAA | TTTTAAATTG | GTCCTCCAAA | AAAATAGGCC | 120 |
| TACCATATAA | TTCATTTTTT | TTCTATAATA | AATTAACAGA | ATAATTGGAA | TAGATTATAT | 180 |
| TATCCTTCTA | TTTAAATTAT | TCTGAATAAA | GAGGAGGAGA | GTGAGTAATG | ATGAGGAAAA | 240 |
| AGAGTTTTTG | GCTTGGCATG | CTGCTCATGA | CACTGGCATT | GTTCATTATA | GGAAACACGA | 300 |
| CTGCTGCTGA | TGATTATTCA | GTTGTAGAGG | AGCATGGGCA | ATTAAGTATT | AGTAACGGAG | 360 |
| AATTAGTCAA | TGATCGAGGC | GAACCAGTTC | AGTTAAAAGG | GATGAGTTCC | CATGGTTTAC | 420 |
| AATGGTACGG | TCAATTTGTA | AACTATGAAA | GCATGAAATG | GCTAAGAGAT | GATTGGGGTA | 480 |
| TAACTGTATT | CCGAGCAGCG | ATGTATACAT | CTTCGGGAGG | ATATATTGAG | GATCCTTCCG | 540 |
| TAAAGGAAAA | AGTAAAAGAG | GCTGTTGAGG | CTGCGATAGA | CCTTGGTATA | TATGTCATAA | 600 |
| TTGATTGGCA | CATCCTTTCA | GACAATGACC | CGAATATATA | TAAAGAAGAA | GCAAAGGATT | 660 |
| TCTTTGATGA | AATGTCTGAG | CTGTATGGAG | ATTACCCGAA | TGTGATATAC | GAAATTGCAA | 720 |
| ATGAACCGAA | TGGTAGTGAT | GTTACGTGGG | ACAATCAAAT | AAAACCGTAT | GCAGAGGAAG | 780 |
| TAATTCCGGT | TATCCGTAAC | AATGATCCTA | ATAACATTAT | TATTGTAGGT | ACAGGTACAT | 840 |
| GGAGTCAGGA | TGTTCATCAT | GCTGCTGATA | ATCAGTTAAC | AGATCCGAAC | GTCATGTATG | 900 |
| CATTTCATTT | TTATGCAGGA | ACACATGGAC | AAAATTTACG | AGACCAAGTA | GATTATGCAT | 960 |
| TAGATCAAGG | AGCAGCAATA | TTTGTTAGTG | AATGGGGAAC | GAGTGAAGCT | ACTGGTGATG | 1020 |
| GCGGCGTGTT | TTTAGATGAA | GCACAAGTGT | GGATTGACTT | TATGGATGAA | AGAAATTTAA | 1080 |
| GCTGGGCAAA | CTGGTCTCTA | ACGCACAAAG | ATGAGTCATC | TGCGGCGTTA | ATGCCAGGTG | 1140 |
| CAAGCCCAAC | TGGTGGGTGG | ACAGAGGCTG | AACTATCTCC | ATCTGGGACA | TTTGTGAGGG | 1200 |
| AAAAAATAAG | AGAGTCAGCA | ACAACACCAC | CTAGTGATCC | AACACCACCA | TCTGATCCAG | 1260 |
| ATCCAGGTGA | ACCAGAACCA | GATCCAGGTG | AACCGGATCC | AACGCCACCA | AGTGATCCAG | 1320 |
| GAGATTATCC | GGCATGGGAT | CCAAATACAA | TTTATACAGA | TGAAATTGTG | TACCATAACG | 1380 |
| GCCAGCTATG | GCAAGCAAAA | TGGTGGACGC | AAAATCAAGA | GCCAGGCGAC | CCATACGGTC | 1440 |
| CGTGGGAACC | ACTCAATTAA | CGATATAATG | ATAGAAATTT | ACTAATGATA | TAAGGAGAAT | 1500 |
| GCCAAGAGTC | TAAATTGGAC | GATTGGCATT | CTCATGGTAC | CTATTAGAGC | TC | 1552 |

(2) INFORMATION FOR SEQ ID NO:2:

(i) SEQUENCE CHARACTERISTICS:
    (A) LENGTH: 1555 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc = "Bacterial DNA"

(vii) IMMEDIATE SOURCE:
    (B) CLONE: P300CELB Fusion Construct #2

(xi) SEQUENCE DESCRIPTION: SEQ ID NO:2:

| | | | | | | |
|---|---|---|---|---|---|---|
| CTCGGGACCT | CTTTCCCTGC | CAGGCTGAAG | CGGTCTATTC | ATACTTTCGA | ACTGAACATT | 60 |

| | | | | | |
|---|---|---|---|---|---|
| TTTCTAAAAC | AGTTATTAAT | AACCAAAAAA | TTTTAAATTG | GTCCTCCAAA | AAAATAGGCC | 120 |
| TACCATATAA | TTCATTTTTT | TTCTATAATA | AATTAACAGA | ATAATTGGAA | TAGATTATAT | 180 |
| TATCCTTCTA | TTTAAATTAT | TCTGAATAAA | GAGGAGGAGA | GTGAGTAATG | ATGAGGAAAA | 240 |
| AGATCTCTAC | TATTTTGTC | GTATTGCTCA | TGACACTGGC | ATTGTTCATT | ATAGGAAACA | 300 |
| CGACTGCTGC | TGATGATTAT | TCAGTTGTAG | AGGAGCATGG | GCAATTAAGT | ATTAGTAACG | 360 |
| GAGAATTAGT | CAATGATCGA | GGCGAACCAG | TTCAGTTAAA | AGGGATGAGT | TCCCATGGTT | 420 |
| TACAATGGTA | CGGTCAATTT | GTAAACTATG | AAAGCATGAA | ATGGCTAAGA | GATGATTGGG | 480 |
| GTATAACTGT | ATTCCGAGCA | GCGATGTATA | CATCTTCGGG | AGGATATATT | GAGGATCCTT | 540 |
| CCGTAAAGGA | AAAAGTAAAA | GAGGCTGTTG | AGGCTGCGAT | AGACCTTGGT | ATATATGTCA | 600 |
| TAATTGATTG | GCACATCCTT | TCAGACAATG | ACCCGAATAT | ATATAAAGAA | GAAGCAAAGG | 660 |
| ATTTCTTTGA | TGAAATGTCT | GAGCTGTATG | GAGATTACCC | GAATGTGATA | TACGAAATTG | 720 |
| CAAATGAACC | GAATGGTAGT | GATGTTACGT | GGGACAATCA | AATAAAACCG | TATGCAGAGG | 780 |
| AAGTAATTCC | GGTTATCCGT | AACAATGATC | CTAATAACAT | TATTATTGTA | GGTACAGGTA | 840 |
| CATGGAGTCA | GGATGTTCAT | CATGCTGCTG | ATAATCAGTT | AACAGATCCG | AACGTCATGT | 900 |
| ATGCATTTCA | TTTTTATGCA | GGAACACATG | GACAAAATTT | ACGAGACCAA | GTAGATTATG | 960 |
| CATTAGATCA | AGGAGCAGCA | ATATTTGTTA | GTGAATGGGG | AACGAGTGAA | GCTACTGGTG | 1020 |
| ATGGCGGCGT | GTTTTAGAT | GAAGCACAAG | TGTGGATTGA | CTTTATGGAT | GAAAGAAATT | 1080 |
| TAAGCTGGGC | AAACTGGTCT | CTAACGCACA | AAGATGAGTC | ATCTGCGGCG | TTAATGCCAG | 1140 |
| GTGCAAGCCC | AACTGGTGGG | TGGACAGAGG | CTGAACTATC | TCCATCTGGG | ACATTTGTGA | 1200 |
| GGGAAAAAAT | AAGAGAGTCA | GCAACAACAC | CACCTAGTGA | TCCAACACCA | CCATCTGATC | 1260 |
| CAGATCCAGG | TGAACCAGAA | CCAGATCCAG | GTGAACCGGA | TCCAACGCCA | CCAAGTGATC | 1320 |
| CAGGAGATTA | TCCGGCATGG | GATCCAAATA | CAATTTATAC | AGATGAAATT | GTGTACCATA | 1380 |
| ACGGCCAGCT | ATGGCAAGCA | AAATGGTGGA | CGCAAAATCA | AGAGCCAGGC | GACCCATACG | 1440 |
| GTCCGTGGGA | ACCACTCAAT | TAACGATATA | ATGATAGAAA | TTTACTAATG | ATATAAGGAG | 1500 |
| AATGCCAAGA | GTCTAAATTG | GACGATTGGC | ATTCTCATGG | TACCTATTAG | AGCTC | 1555 |

( 2 ) INFORMATION FOR SEQ ID NO:3:

( i ) SEQUENCE CHARACTERISTICS:
        ( A ) LENGTH: 1558 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Bacterial DNA"

( v i i ) IMMEDIATE SOURCE:
        ( B ) CLONE: P300CELB Fusion Construct #3

( x i ) SEQUENCE DESCRIPTION: SEQ ID NO:3:

| | | | | | |
|---|---|---|---|---|---|
| CCCGGGACCT | CTTTCCCTGC | CAGGCTGAAG | CGGTCTATTC | ATACTTTCGA | ACTGAACATT | 60 |
| TTTCTAAAAC | AGTTATTAAT | AACCAAAAAA | TTTTAAATTG | GTCCTCCAAA | AAAATAGGCC | 120 |
| TACCATATAA | TTCATTTTTT | TTCTATAATA | AATTAACAGA | ATAATTGGAA | TAGATTATAT | 180 |
| TATCCTTCTA | TTTAAATTAT | TCTGAATAAA | GAGGAGGAGA | GTGAGTAATG | ATGAGGAAAA | 240 |
| AGAGTTTTTG | GCTTGGGATG | CTGACGGCCT | TCATGCTCGT | GTTCACGATG | GCATTCAGCG | 300 |
| ATTCCGCTTC | TGCAGATGAT | TATTCAGTTG | TAGAGGAGCA | TGGGCAATTA | AGTATTAGTA | 360 |

-continued

| | | | | | |
|---|---|---|---|---|---|
| ACGGAGAATT | AGTCAATGAT | CGAGGCGAAC | CAGTTCAGTT | AAAAGGGATG | AGTTCCCATG | 420 |
| GTTTACAATG | GTACGGTCAA | TTTGTAAACT | ATGAAAGCAT | GAAATGGCTA | AGAGATGATT | 480 |
| GGGGTATAAC | TGTATTCCGA | GCAGCGATGT | ATACATCTTC | GGGAGGATAT | ATTGAGGATC | 540 |
| CTTCCGTAAA | GGAAAAAGTA | AAAGAGGCTG | TTGAGGCTGC | GATAGACCTT | GGTATATATG | 600 |
| TCATAATTGA | TTGGCACATC | CTTTCAGACA | ATGACCCGAA | TATATATAAA | GAAGAAGCAA | 660 |
| AGGATTTCTT | TGATGAAATG | TCTGAGCTGT | ATGGAGATTA | CCCGAATGTG | ATATACGAAA | 720 |
| TTGCAAATGA | ACCGAATGGT | AGTGATGTTA | CGTGGGACAA | TCAAATAAAA | CCGTATGCAG | 780 |
| AGGAAGTAAT | TCCGGTTATC | CGTAACAATG | ATCCTAATAA | CATTATTATT | GTAGGTACAG | 840 |
| GTACATGGAG | TCAGGATGTT | CATCATGCTG | CTGATAATCA | GTTAACAGAT | CCGAACGTCA | 900 |
| TGTATGCATT | TCATTTTTAT | GCAGGAACAC | ATGGACAAAA | TTTACGAGAC | CAAGTAGATT | 960 |
| ATGCATTAGA | TCAAGGAGCA | GCAATATTTG | TTAGTGAATG | GGGAACGAGT | GAAGCTACTG | 1020 |
| GTGATGGCGG | CGTGTTTTTA | GATGAAGCAC | AAGTGTGGAT | TGACTTTATG | GATGAAAGAA | 1080 |
| ATTTAAGCTG | GGCAAACTGG | TCTCTAACGC | ACAAAGATGA | GTCATCTGCG | GCGTTAATGC | 1140 |
| CAGGTGCAAG | CCCAACTGGT | GGGTGGACAG | AGGCTGAACT | ATCTCCATCT | GGGACATTTG | 1200 |
| TGAGGGAAAA | AATAAGAGAG | TCAGCAACAA | CACCACCTAG | TGATCCAACA | CCACCATCTG | 1260 |
| ATCCAGATCC | AGGTGAACCA | GAACCAGATC | CAGGTGAACC | GGATCCAACG | CCACCAAGTG | 1320 |
| ATCCAGGAGA | TTATCCGGCA | TGGGATCCAA | ATACAATTTA | TACAGATGAA | ATTGTGTACC | 1380 |
| ATAACGGCCA | GCTATGGCAA | GCAAAATGGT | GGACGCAAAA | TCAAGAGCCA | GGCGACCCAT | 1440 |
| ACGGTCCGTG | GGAACCACTC | AATTAACGAT | ATAATGATAG | AAATTTACTA | ATGATATAAG | 1500 |
| GAGAATGCCA | AGAGTCTAAA | TTGGACGATT | GGCATTCTCA | TGGTACCTAT | TAGAGCTC | 1558 |

( 2 ) INFORMATION FOR SEQ ID NO:4:

( i ) SEQUENCE CHARACTERISTICS:
        ( A ) LENGTH: 1542 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Bacterial DNA"

( v i i ) IMMEDIATE SOURCE:
        ( B ) CLONE: P300CELB Fusion Construct #4

( x i ) SEQUENCE DESCRIPTION: SEQ ID NO:4:

| | | | | | |
|---|---|---|---|---|---|
| CTCGGGACCT | CTTTCCCTGC | CAGGCTGAAG | CGGTCTATTC | ATACTTTCGA | ACTGAACATT | 60 |
| TTTCTAAAAC | AGTTATTAAT | AACCAAAAAA | TTTTAAATTG | GTCCTCCAAA | AAAATAGGCC | 120 |
| TACCATATAA | TTCATTTTTT | TTCTATAATA | AATTAACAGA | ATAATTGGAT | CCTTCTATTT | 180 |
| AAATTATTCT | GAATAAAGAG | GAGGAGAGTG | AGTAATGATG | AGGAAAAAGA | GTTTTTGGCT | 240 |
| TGGGATGCTG | ACGGCCTTCA | TGCTCGTGTT | CACGATGGCA | TCGATCGCAT | CGGCTGCAGA | 300 |
| TGATTATTCA | GTTGTAGAGG | AGCATGGGCA | ATTAAGTATT | AGTAACGGAG | AATTAGTCAA | 360 |
| TGATCGAGGC | GAACCAGTTC | AGTTAAAAGG | GATGAGTTCC | CATGGTTTAC | AATGGTACGG | 420 |
| TCAATTTGTA | AACTATGAAA | GCATGAAATG | GCTAAGAGAT | GATTGGGGTA | TAACTGTATT | 480 |
| CCGAGCAGCG | ATGTATACAT | CTTCGGGAGG | ATATATTGAG | GATCCTTCCG | TAAAGGAAAA | 540 |
| AGTAAAAGAG | GCTGTTGAGG | CTGCGATAGA | CCTTGGTATA | TATGTCATAA | TTGATTGGCA | 600 |
| CATCCTTTCA | GACAATGACC | CGAATATATA | TAAAGAAGAA | GCAAAGGATT | TCTTTGATGA | 660 |
| AATGTCTGAG | CTGTATGGAG | ATTACCCGAA | TGTGATATAC | GAAATTGCAA | ATGAACCGAA | 720 |

| | | | | | | |
|---|---|---|---|---|---|---|
| TGGTAGTGAT | GTTACGTGGG | ACAATCAAAT | AAAACCGTAT | GCAGAGGAAG | TAATTCCGGT | 780 |
| TATCCGTAAC | AATGATCCTA | ATAACATTAT | TATTGTAGGT | ACAGGTACAT | GGAGTCAGGA | 840 |
| TGTTCATCAT | GCTGCTGATA | ATCAGTTAAC | AGATCCGAAC | GTCATGTATG | CATTTCATTT | 900 |
| TTATGCAGGA | ACACATGGAC | AAAATTTACG | AGACCAAGTA | GATTATGCAT | TAGATCAAGG | 960 |
| AGCAGCAATA | TTTGTTAGTG | AATGGGGAAC | GAGTGAAGCT | ACTGGTGATG | GCGGCGTGTT | 1020 |
| TTTAGATGAA | GCACAAGTGT | GGATTGACTT | TATGGATGAA | AGAAATTTAA | GCTGGGCAAA | 1080 |
| CTGGTCTCTA | ACGCACAAAG | ATGAGTCATC | TGCGGCGTTA | ATGCCAGGTG | CAAGCCCAAC | 1140 |
| TGGTGGGTGG | ACAGAGGCTG | AACTATCTCC | ATCTGGACA | TTTGTGAGGG | AAAAAATAAG | 1200 |
| AGAGTCAGCA | ACAACACCAC | CTAGTGATCC | AACACCACCA | TCTGATCCAG | ATCCAGGTGA | 1260 |
| ACCAGAACCA | GATCCAGGTG | AACCGGATCC | AACGCCACCA | AGTGATCCAG | GAGATTATCC | 1320 |
| GGCATGGGAT | CCAAATACAA | TTTATACAGA | TGAAATTGTG | TACCATAACG | GCCAGCTATG | 1380 |
| GCAAGCAAAA | TGGTGGACGC | AAAATCAAGA | GCCAGGCGAC | CCATACGGTC | CGTGGGAACC | 1440 |
| ACTCAATTAA | CGATATAATG | ATAGAAATTT | ACTAATGATA | TAAGGAGAAT | GCCAAGAGTC | 1500 |
| TAAATTGGAC | GATTGGCATT | CTCATGGTAC | CTATTAGAGC | TC | | 1542 |

( 2 ) INFORMATION FOR SEQ ID NO:5:

( i ) SEQUENCE CHARACTERISTICS:
        ( A ) LENGTH: 5390 base pairs
        ( B ) TYPE: nucleic acid
        ( C ) STRANDEDNESS: double
        ( D ) TOPOLOGY: circular ( i i ) MOLECULE TYPE: other nucleic acid
        ( A ) DESCRIPTION: /desc = "Bacterial Plasmid DNA"

( v i i ) IMMEDIATE SOURCE:
        ( B ) CLONE: C4TET Plasmid Construct ( x i ) SEQUENCE DESCRIPTION: SEQ ID NO:5:

| | | | | | | |
|---|---|---|---|---|---|---|
| CTTAAGGAAC | GTACAGACGG | CTTAAAAGCC | TTTAAAAACG | TTTTTAAGGG | GTTTGTAGAC | 60 |
| AAGGTAAAGG | ATAAAACAGC | ACAATTCCAA | GAAAAACACG | ATTTAGAACC | TAAAAAGAAC | 120 |
| GAATTTGAAC | TAACTCATAA | CCGAGAGGTA | AAAAAAGAAC | GAAGTCGAGA | TCAGGGAATG | 180 |
| AGTTTATAAA | ATAAAAAAAG | CACCTGAAAA | GGTGTCTTTT | TTTGATGGTT | TTGAACTTGT | 240 |
| TCTTTCTTAT | CTTGATACAT | ATAGAAATAA | CGTCATTTTT | ATTTAGTTG | CTGAAAGGTG | 300 |
| CGTTGAAGTG | TTGGTATGTA | TGTGTTTTAA | AGTATTGAAA | ACCCTTAAAA | TTGGTTGCAC | 360 |
| AGAAAAACCC | CATCTGTTAA | AGTTATAAGT | GACCAAACAA | ATAACTAAAT | AGATGGGGT | 420 |
| TTCTTTTAAT | ATTATGTGTC | CTAATAGTAG | CATTTATTCA | GATGAAAAAT | CAAGGGTTTT | 480 |
| AGTGGACAAG | ACAAAAAGTG | GAAAGTGAG | ACCATGGAGA | GAAAAGAAAA | TCGCTAATGT | 540 |
| TGATTACTTT | GAACTTCTGC | ATATTCTTGA | ATTTAAAAAG | GCTGAAAGAG | TAAAAGATTG | 600 |
| TGCTGAAATA | TTAGAGTATA | AACAAATCG | TGAAACAGGC | GAAAGAAAGT | TGTATCGAGT | 660 |
| GTGGTTTTGT | AAATCCAGGC | TTTGTCCAAT | GTGCAACTGG | AGGAGAGCAA | TGAAACATGG | 720 |
| CATTCAGTCA | CAAAAGGTTG | TTGCTGAAGT | TATTAAACAA | AAGCCAACAG | TTCGTTGGTT | 780 |
| GTTTCTCACA | TTAACAGTTA | AAAATGTTTA | TGATGGCGAA | GAATTAAATA | AGAGTTTGTC | 840 |
| AGATATGGCT | CAAGGATTTC | GCCGAATGAT | GCAATATAAA | AAATTAATA | AAAATCTTGT | 900 |
| TGGTTTTATG | CGTGCAACGG | AAGTGACAAT | AAATAATAAA | GATAATTCTT | ATAATCAGCA | 960 |
| CATGCATGTA | TTGGTATGTG | TGGAACCAAC | TTATTTTAAG | AATACAGAAA | ACTACGTGAA | 1020 |

-continued

| | | | | | | |
|---|---|---|---|---|---|---|
| TCAAAAACAA | TGGATTCAAT | TTTGGAAAAA | GGCAATGAAA | TTAGACTATG | ATCCAAATGT | 1080 |
| AAAAGTTCAA | ATGATTCGAC | CGAAAAATAA | ATATAAATCG | GATATACAAT | CGGCAATTGA | 1140 |
| CGAAACTGCA | AAATATCCTG | TAAAGGATAC | GGATTTTATG | ACCGATGATG | AAGAAAAGAA | 1200 |
| TTTGAAACGT | TTGTCTGATT | TGGAGGAAGG | TTTACACCGT | AAAAGGTTAA | TCTCCTATGG | 1260 |
| TGGTTTGTTA | AAAGAAATAC | ATAAAAAATT | AAACCTTGAT | GACACAGAAG | AAGGCGATTT | 1320 |
| GATTCATACA | GATGATGACG | AAAAAGCCGA | TGAAGATGGA | TTTTCTATTA | TTGCAATGTG | 1380 |
| GAATTGGGAA | CGGAAAAATT | ATTTTATTAA | AGAGTAGTTC | AACAAACGGG | CCATATTGTT | 1440 |
| GTATAAGTGA | TGAAATACTG | AATTTAAAAC | TTAGTTTATA | TGTGGTAAAA | TGTTTTAATC | 1500 |
| AAGTTTAGGA | GGAATTAATT | ATGAAGTGTA | ATGAATGTAA | CAGGGTTCAA | TTAAAAGAGG | 1560 |
| GAAGCGTATC | ATTAACCCTA | TAAACTACGT | CTGCCCTCAT | TATTGGAGGG | TGAAATGTGA | 1620 |
| ATACATCCTA | TTCACAATCG | AATTTACGAC | ACAACCAAAT | TTTAATTTGG | CTTTGCATTT | 1680 |
| TATCTTTTTT | TAGCGTATTA | AATGAAATGG | TTTTGAACGT | CTCATTACCT | GATATTGCAA | 1740 |
| ATGATTTTAA | TAAACCACCT | GCGAGTACAA | ACTGGGTGAA | CACAGCCTTT | ATGTTAACCT | 1800 |
| TTTCCATTGG | AACAGCTGTA | TATGGAAAGC | TATCTGATCA | ATTAGGCATC | AAAAGGTTAC | 1860 |
| TCCTATTTGG | AATTATAATA | AATTGTTTCG | GGTCGGTAAT | TGGGTTTGTT | GGCCATTCTT | 1920 |
| TCTTTTCCTT | ACTTATATG | GCTCGTTTTA | TTCAAGGGGC | TGGTGCAGCT | GCATTCCAG | 1980 |
| CACTCGTAAT | GGTTGTAGTT | GCGCGCTATA | TTCCAAAGGA | AAATAGGGGT | AAAGCATTTG | 2040 |
| GTCTTATTGG | ATCGATAGTA | GCCATGGGAG | AAGGAGTCGG | TCCAGCGATT | GGTGGAATGA | 2100 |
| TAGCCCATTA | TATTCATTGG | TCCTATCTTC | TACTCATTCC | TATGATAACA | ATTATCACTG | 2160 |
| TTCCGTTTCT | TATGAAATTA | TTAAAGAAAG | AAGTAAGGAT | AAAAGGTCAT | TTTGATATCA | 2220 |
| AAGGAATTAT | ACTAATGTCT | GTAGGCATTG | TATTTTTTAT | GTTGTTTACA | ACATCATATA | 2280 |
| GCATTTCTTT | TCTTATCGTT | AGCGTGCTGT | CATTCCTGAT | ATTTGTAAAA | CATATCAGGA | 2340 |
| AAGTAACAGA | TCCTTTTGTT | GATCCCGGAT | TAGGGAAAAA | TATACCTTTT | ATGATTGGAG | 2400 |
| TTCTTTGTGG | GGGAATTATA | TTTGGAACAG | TAGCAGGGTT | TGTCTCTATG | GTTCCTTATA | 2460 |
| TGATGAAAGA | TGTTCACCAG | CTAAGTACTG | CCGAAATCGG | AAGTGTAATT | ATTTTCCCTG | 2520 |
| GAACAATGAG | TGTCATTATT | TTCGGCTACA | TTGGTGGGAT | ACTTGTTGAT | AGAAGAGGTC | 2580 |
| CTTTATACGT | GTTAAACATC | GGAGTTACAT | TTCTTTCTGT | TAGCTTTTA | ACTGCTTCCT | 2640 |
| TTCTTTTAGA | AACAACATCA | TGGTTCATGA | CAATTATAAT | CGTATTTGTT | TTAGGTGGGC | 2700 |
| TTTCGTTCAC | CAAAACAGTT | ATATCAACAA | TTGTTTCAAG | TAGCTTGAAA | CAGCAGGAAG | 2760 |
| CTGGTGCTGG | AATGAGTTTG | CTTAACTTTA | CCAGCTTTTT | ATCAGAGGGA | ACAGGTATTG | 2820 |
| CAATTGTAGG | TGGTTTATTA | TCCATACCCT | TACTTGATCA | AAGGTTGTTA | CCTATGGAAG | 2880 |
| TTGATCAGTC | AACTTATCTG | TATAGTAATT | TGTTATTACT | TTTTTCAGGA | ATCATTGTCA | 2940 |
| TTAGTTGGCT | GGTTACCTTG | AATGTATATA | AACATTCTCA | AAGGGATTTC | TAAATCGTTA | 3000 |
| AGGGATCAAC | TTTGGGAGAG | AGTTCAAAAT | TGATCCTTTT | TTTATAACAG | GAATTCAAAT | 3060 |
| CTTTTTGTTC | CATTAAAGGG | CGCGATTGCT | GAATAAAAGA | TACGAGAGAC | CTCTCTTGTA | 3120 |
| TCTTTTTTAT | TTGAGTGGT | TTGTCCGTT | ACACTAGAAA | ACCGAAAGAC | AATAAAAATT | 3180 |
| TTATTCTTGC | TGAGTCTGGC | TTTCGGTAAG | CTAGACAAAA | CGGACAAAAT | AAAAATTGGC | 3240 |
| AAGGGTTTAA | AGGTGGAGAT | TTTTTGAGTG | ATCTTCTCAA | AAAATACTAC | CTGTCCCTTG | 3300 |
| CTGATTTTTA | AACGAGCACG | AGAGCAAAAC | CCCCCTTTGC | TGAGGTGGCA | GAGGGCAGGT | 3360 |
| TTTTTTGTTT | CTTTTTTCTC | GTAAAAAAAA | GAAAGGTCTT | AAAGGTTTTA | TGGTTTTGGT | 3420 |

-continued

| | | | | | | |
|---|---|---|---|---|---|---|
| CGGCACTGCC | GACAGCCTCG | CAGAGCACAC | ACTTTATGAA | TATAAAGTAT | AGTGTGTTAT | 3480 |
| ACTTTACTTG | GAAGTGGTTG | CCGGAAAGAG | CGAAAATGCC | TCACATTTGT | GCCACCTAAA | 3540 |
| AAGGAGCGAT | TTACATATGA | GTTATGCAGT | TTGTAGAATG | CAAAAAGTGA | AATCAGCTGG | 3600 |
| ACTAAAAGGC | ATGCAATTTC | ATAATCAAAG | AGAGCGAAAA | AGTAGAACGA | ATGATGATAT | 3660 |
| TGACCATGAG | CGAACACGTG | AAAATTATGA | TTTGAAAAAT | GATAAAAATA | TTGATTACAA | 3720 |
| CGAACGTGTC | AAAGAATTA | TTGAATCACA | AAAAACAGGT | ACAAGAAAAA | CGAGGAAAGA | 3780 |
| TGCTGTTCTT | GTAAATGAGT | TGCTAGTAAC | ATCTGACCGA | GATTTTTTG | AGCAACTGGA | 3840 |
| TCCTCGGGAC | CTCTTTCCCT | GCCAGGCTGA | AGCGGTCTAT | TCATACTTTC | GAACTGAACA | 3900 |
| TTTTTCTAAA | ACAGTTATTA | ATAACCAAAA | AATTTTAAAT | TGGTCCTCCA | AAAAAATAGG | 3960 |
| CCTACCATAT | AATTCATTTT | TTTTCTATAA | TAAATTAACA | GAATAATTGG | ATCCTTCTAT | 4020 |
| TTAAATTATT | CTGAATAAAG | AGGAGGAGAG | TGAGTAATGA | TGAGGAAAAA | GAGTTTTGG | 4080 |
| CTTGGGATGC | TGACGGCCTT | CATGCTCGTG | TTCACGATGG | CATCGATCGC | ATCGGCTGCA | 4140 |
| GATGATTATT | CAGTTGTAGA | GGAGCATGGG | CAATTAAGTA | TTAGTAACGG | AGAATTAGTC | 4200 |
| AATGATCGAG | GCGAACCAGT | TCAGTTAAAA | GGGATGAGTT | CCCATGGTTT | ACAATGGTAC | 4260 |
| GGTCAATTTG | TAAACTATGA | AAGCATGAAA | TGGCTAAGAG | ATGATTGGGG | TATAACTGTA | 4320 |
| TTCCGAGCAG | CGATGTATAC | ATCTTCGGGA | GGATATATTG | AGGATCCTTC | CGTAAAGGAA | 4380 |
| AAAGTAAAAG | AGGCTGTTGA | GGCTGCGATA | GACCTTGGTA | TATATGTCAT | AATTGATTGG | 4440 |
| CACATCCTTT | CAGACAATGA | CCCGAATATA | TATAAAGAAG | AAGCAAAGGA | TTTCTTTGAT | 4500 |
| GAAATGTCTG | AGCTGTATGG | AGATTACCCG | AATGTGATAT | ACGAAATTGC | AAATGAACCG | 4560 |
| AATGGTAGTG | ATGTTACGTG | GGACAATCAA | ATAAAACCGT | ATGCAGAGGA | AGTAATTCCG | 4620 |
| GTTATCCGTA | ACAATGATCC | TAATAACATT | ATTATTGTAG | GTACAGGTAC | ATGGAGTCAG | 4680 |
| GATGTTCATC | ATGCTGCTGA | TAATCAGTTA | ACAGATCCGA | ACGTCATGTA | TGCATTTCAT | 4740 |
| TTTTATGCAG | GAACACATGG | ACAAAATTTA | CGAGACCAAG | TAGATTATGC | ATTAGATCAA | 4800 |
| GGAGCAGCAA | TATTTGTTAG | TGAATGGGGA | ACGAGTGAAG | CTACTGGTGA | TGGCGGCGTG | 4860 |
| TTTTTAGATG | AAGCACAAGT | GTGGATTGAC | TTTATGGATG | AAAGAAATTT | AAGCTGGGCA | 4920 |
| AACTGGTCTC | TAACGCACAA | AGATGAGTCA | TCTGCGGCGT | TAATGCCAGG | TGCAAGCCCA | 4980 |
| ACTGGTGGGT | GGACAGAGGC | TGAACTATCT | CCATCTGGGA | CATTTGTGAG | GGAAAAAATA | 5040 |
| AGAGAGTCAG | CAACAACACC | ACCTAGTGAT | CCAACACCAC | CATCTGATCC | AGATCCAGGT | 5100 |
| GAACCAGAAC | CAGATCCAGG | TGAACCGGAT | CCAACGCCAC | CAAGTGATCC | AGGAGATTAT | 5160 |
| CCGGCATGGG | ATCCAAATAC | AATTTATACA | GATGAAATTG | TGTACCATAA | CGGCCAGCTA | 5220 |
| TGGCAAGCAA | AATGGTGGAC | GCAAAATCAA | GAGCCAGGCG | ACCCATACGG | TCCGTGGGAA | 5280 |
| CCACTCAATT | AACGATATAA | TGATAGAAAT | TTACTAATGA | TATAAGGAGA | ATGCCAAGAG | 5340 |
| TCTAAATTGG | ACGATTGGCA | TTCTCATGGT | ACCTATTAGA | GCTCGAATTC | | 5390 |